United States Patent [19]

Downing

[11] 4,440,783
[45] Apr. 3, 1984

[54] COMPOSITION FOR REPELLING ANIMALS FROM GARBAGE AND THE LIKE

[75] Inventor: Harry M. Downing, Hewitt, N.J.

[73] Assignees: Bernard Weiss, New York, N.Y.; Jonathan J. Stern, Upper Saddle River, N.J.; Burt B. Houseworth, Elmsford, N.Y.

[21] Appl. No.: 469,228

[22] Filed: Feb. 24, 1983

[51] Int. Cl.$^3$ ............................................. A01M 47/46
[52] U.S. Cl. ..................................................... 424/302
[58] Field of Search ............................ 424/84, 302, 45

[56] References Cited

U.S. PATENT DOCUMENTS

| | | | |
|---|---|---|---|
| 3,113,908 | 12/1963 | Pieroh et al. | 424/302 |
| 3,663,253 | 5/1972 | Stone | 424/195 |
| 3,686,255 | 8/1972 | Knowles | 424/322 |
| 3,900,560 | 8/1975 | Jacobson | 424/45 |
| 3,923,997 | 12/1975 | Meuly | 424/45 |
| 4,164,561 | 8/1979 | Hautmann | 424/46 |

FOREIGN PATENT DOCUMENTS 51-19129  2/1976  Japan ....................................... 424/45

OTHER PUBLICATIONS

*Codex Vegetabilis*, E. F. Steinmetz, 89, 90, 1957.
Chem. Abstracts 78:136299x, 1973.

*Primary Examiner*—Albert T. Meyers
*Assistant Examiner*—John M. Kilcoyne
*Attorney, Agent, or Firm*—Robert I. Pearlman

[57] ABSTRACT

A chemical composition for warding off racoons, dogs and the like from garbage comprising a combination of chemical agents including a member of the isothiocyanate family (commonly referred to as mustard oil), preferably allyl isothiocyanate.

The combination of mustard oil with lemon grass oil together with masking agents is particularly preferred so that the composition as applied to household garbage and receptacles is not unpleasant to human smell while nevertheless repulsive to foraging animals.

In addition to use about homes, restaurants and the like, the present composition may be used at camp sites for similar purposes.

9 Claims, No Drawings

COMPOSITION FOR REPELLING ANIMALS FROM GARBAGE AND THE LIKE

BACKGROUND OF THE INVENTION

The present invention relates to repelling animals such as racoons and dogs from garbage as might be dispensed from a household or restaurant. In particular it relates to a composition which when applied to the garbage, preferably by spraying, will repel the animals while nevertheless being acceptable to humans from both an odor and safety viewpoint.

It is a common problem in urban, suburban and less populated areas to have animals foraging in garbage cans and refuse holders used for disposal of the normal accumulation of garbage from households, restaurants and other establishments. This is also a problem at camp sites where animals are attracted by leftovers. Typically such animals are dogs, racoons or cats as well as other possible creatures in less urban areas. The racoon in particular has been known to be both tenacious and clever in getting at garbage even when maintained in covered receptacles.

Due to the long standing nature of this problem one might expect that an effective solution would be in common use. This is not the case. During experimentation it has been found that many chemicals and extracts of plants which might have been expected to repel the animals were not effective for such use. Examples included cinnamic aldehyde, peppermint oil, methyl salicylate and benzaldehyde, among many others.

The inventor is not aware of any commercial product presently sold for this purpose. U.S. Pat. No. 3,686,255 discloses applying cyclohexyl compounds and certain substituted cyclohexyl isocyanates and thiocyanates to an animal or its habitat as a repellent.

SUMMARY OF THE INVENTION

The present invention provides an effective composition serving to repel animals such as racoons, dogs and the like from garbage while at the same time being acceptable to humans in terms of both safety and odor. More particularly the present composition contains as its active agent a minor concentration of mustard oil or its alkyl derivatives. More specifically the present compositions have as its key ingredient allyl isothiocyanates (mustard oil) or the alkyl derivatives thereof, particularly a $C_1$ to $C_4$ alkyl isothiocyanates. While allyl isothiocyanate is preferred, methyl, ethyl, propyl, butyl and isobutyl isothiocyanates may also be used.

Typically the foregoing isothiocyanate will range from 0.25% to 25%, preferably 1% to 10% by weight of the active portion of the composition. The "active portion of the composition" denotes the portion of the total composition having chemicals with an effect on the odor (either to repel the animals or to make the composition more acceptable to humans), in contrast to diluents, propellents, fixatives, or additives relating simply to the form of applying the composition.

It is particularly preferred to utilize said isothiocyanate in combination with lemon grass oil, the latter normally being present in significantly greater amounts.

In addition, the present compositions may contain other ingredients adding to the repellent effective on the animals, together with suitable odor masking chemicals such as methyl salicylate, pine oil, terpineol, benzaldehyde, ethyl acetate, amyl acetate and other odor masking agents well known to those skilled in the art.

Since it is preferred to administer the present compositions as a mist or spray, the compositions will also contain suitable liquid diluents such as water, kerosene, propane, isobutane and other hydrocarbons and alcohols; emulsifiers (detergents), and other liquids generally found in household spray formulations or pharmaceutical preparations so as to be acceptable from a human safety viewpoint. These materials are the "nonactive portion" of the present compositions and typically are the major percentage of the overall compositions, e.g., 75 to 99 percent, typically 90 to 98 weight percent.

In addition to the foregoing components of the composition, the present composition may also contain:
(1) Fixative agents, such as shown below, which slow down evaporation rates. Such fixative agents generally comprise 0 to 100, preferably 20 to 60 weight percent of the active portion of the composition.
   (a) Glycols, such as propylene glycol, diethylene glycol, dipropylene glycol and the like.
   (b) Resins, such as pine resin, acrylic resin, etc.
(2) Antioxidants, such as sodium nitrate, to extend the stability of both the composition and its container.

While it is preferred to apply the composition in the form of a spray by either an aerosol container or pump spray device, it can be applied as a liquid. The former is preferred as covering a greater area of garbage with a smaller amount of composition.

Typical components of the present composition are summarized in the following Table A. All percentages are on a weight percent basis:

TABLE A

|  | Weight Percentages | | |
| --- | --- | --- | --- |
|  | Broad Range | Preferred Range | Most Desired |
| Overall Composition |  |  |  |
| Active Portion | 1 to 25 | 2 to 10 | 4 to 8 |
| Inactive Portion | 75 to 99 | 90 to 98 | 92 to 96 |
| Components of Active Portion[1] |  |  |  |
| Allyl or alkyl isothiocyanate | 1 to 20 | 2 to 10 | 2 to 5 |
| Lemon grass oil | 0 to 70 | 25 to 50 | 30 to 45 |
| Masking agent | 10 to 80 | 20 to 70 | 30 to 60 |

[1]Percentage based on active portion only

EXAMPLES

A series of experiments was run to test the effectiveness of some 40 plus chemical agents as a means of repelling animals from garbage. In these tests two drops of the chemical agent to be tested was placed on an ounce of hamburger meat and spread around its top surface. In a given test one to three pieces of hamburger meat (each 1 ounce) thus chemically treated was placed outdoors overnight together with one or two one ounce pieces of hamburger meat which had not be treated. The tests were conducted at a household bordering a wooded area in suburban New Jersey.

The lack of effectiveness of various agents thus tested was evidenced by the fact that hamburger meat impregnated with such agents were not found the next day as were the untreated hamburger meat. This was due to animal foraging overnight and illustrated the lack of effectiveness of such agents in repelling the animals. Among the various agents which were not effective as so tested were the following: cinnamic aldehyde, benzoine, peppermint oil, menthol, methyl salicylate, lemon oil, cyclohexane, amyl butyrate, camphor, terpintine and isopropyl alcohol.

In contrast to the foregoing, treating hamburger meat samples with a member of the mustard oil family (i.e. allyl isothiocyanate or lower alkyl derivatives such as propyl isothiocyanate) was found effective in repelling the animals as witnessed by the treated hamburger meat being undisturbed after the overnight exposure. Such isothiocyanates are safe for humans and have been used as flavoring ingredients in foods as well as counterirritants in ointments and mustard plasters. The present compositions do not employ the very high concentrations of mustard gas employed as a military poison gas in warfare and are safe for human exposure during application.

TYPICAL COMPOSITION

When using the present composition as a spray to be dispensed by an aerosol spray container the following typical percentages of ingredients was employed.

TABLE B

|  | Weight Percent of Active Portion |
|---|---|
| Allyl isothiocyanate | 3 |
| Lemon Grass Oil | 40 |
| Lemon Grass Terpenes | 10 |
| Masking Agents, including citronella and pine oil | 47 |

The above composition comprises 5 to 10% of an overall composition which further contains diluents such as water and/or alcohol, and fixatives such as glycols, resins and esters.

Various modifications will suggest themselves to those skilled in the art with respect to the basic concepts described in the specification and claims.

I claim as my invention:

1. A composition for repelling animals from garbage comprising:
   (a) 1 to 25 weight percent of an active portion containing a minor but repellent effective concentration of an isothyocyanate chosen from the group consisting of allyl isothiocyanate and $C_1$ to $C_4$ alkyl isothiocyanate together with an odor masking material for making the composition more acceptable to humans, and
   (b) 75 to 99 weight percent of a non-active liquid diluent portion which comprises the major portion of the overall composition.

2. The composition of claim 1 wherein said isothiocyanate comprises 1 to 20 weight percent of the active portion of said composition.

3. The composition of claim 1 which further contains 25 to 50 weight percent of lemon grass oil in said active portion of said composition.

4. The composition of claim 1 wherein the active portion of the composition contains 2 to 10 weight percent isothiocyanate and 20 to 70 weight percent masking material.

5. The composition of claim 1 containing allyl isothiocyanate.

6. The composition of claim 5 wherein said allyl isothiocyanate compromises 1 to 20 weight percent of said active portion of said composition.

7. The composition of claim 1 wherein said composition contains 2 to 10 weight percent active portion and 90 to 98 weight percent inactive portion.

8. A composition for repelling animals from garbage comprising:
   (a) 1 to 25 weight percent of an active portion containing, based on active portion, 2 to 10 weight percent allyl isothiocyanate, 25 to 50 weight percent lemon grass oil and 20 to 70 weight percent of odor masking material for making the composition more acceptable to humans, and
   (b) 75 to 99 weight percent of non-active liquid diluent portion which comprises the major portion of the overall composition.

9. The composition of claim 8 which further comprises a member of the group consisting of fixatives, and antioxidants.

* * * * *